United States Patent
Mlinar et al.

(10) Patent No.: US 10,703,691 B1
(45) Date of Patent: Jul. 7, 2020

(54) PROCESS FOR PRODUCING PARA-XYLENE USING TWO FEED RAFFINATE COLUMN

(71) Applicant: UOP LLC, Des Plaines, IL (US)

(72) Inventors: Anton Mlinar, Vernon Hills, IL (US);
Nikunj Patel, Melrose Park, IL (US);
Jason L. Noe, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/265,911

(22) Filed: Feb. 1, 2019

(51) Int. Cl.
*C07C 7/12* (2006.01)
*C07C 5/22* (2006.01)
*B01D 15/18* (2006.01)
*C07C 7/04* (2006.01)
*B01D 3/00* (2006.01)
*C07C 15/08* (2006.01)

(52) U.S. Cl.
CPC .............. *C07C 7/12* (2013.01); *B01D 3/009* (2013.01); *B01D 15/1828* (2013.01); *C07C 5/22* (2013.01); *C07C 7/04* (2013.01); *C07C 15/08* (2013.01)

(58) Field of Classification Search
CPC ............. C07C 7/12; C07C 7/13; C07C 7/04
USPC ....................................................... 585/828
See application file for complete search history.

(56) References Cited

U.S. PATENT DOCUMENTS

| | | | |
|---|---|---|---|
| 9,850,186 B2 | 12/2017 | Agrawal et al. | |
| 2002/0143223 A1* | 10/2002 | Leflaive | C07C 7/005 585/820 |
| 2015/0087878 A1 | 3/2015 | Laroche et al. | |
| 2015/0266794 A1 | 9/2015 | Ou et al. | |

* cited by examiner

*Primary Examiner* — Thuan D Dang (57) ABSTRACT

Process for producing para-xylene are described. The processes utilize a dual raffinate approach. Two raffinate streams from the adsorption separation unit are fed to the raffinate distillation column independently to take advantage of the differing desorbent concentrations in the two raffinate streams. The process yields significant reboiler duty savings and a reduction in overall fired fuel needed.

20 Claims, 2 Drawing Sheets

PROCESS FOR PRODUCING PARA-XYLENE USING TWO FEED RAFFINATE COLUMN

BACKGROUND $C_8$ alkylaromatic hydrocarbons are generally considered to be valuable products, with the highest demand being for para-xylene. Major sources of para-xylene include mixed xylene streams that result from the refining of crude oil. Examples of such streams are those resulting from commercial xylene isomerization processes or from the separation of $C_8$ alkylaromatic hydrocarbon fractions derived from a catalytic reformate by liquid-liquid extraction and/or fractional distillation.

A simulated moving bed ("SMB") adsorption process is used commercially in a number of large scale petrochemical separations to recover high purity para-xylene from mixed xylenes. As used herein, the term "mixed xylenes" refers to a mixture of $C_8$ aromatic isomers that includes ethylbenzene, para-xylene, meta-xylene and ortho-xylene. High purity para-xylene may be used for the production of polyester fibers, resins and films by converting para-xylene to terephthalic acid or dimethyl terephthalate, which is then reacted with ethylene glycol to form polyethylene terephthalate, and the raw material for most polyesters.

The general technique employed in the performance of SMB adsorptive separation processes is widely described and practiced. Generally, the process simulates a moving bed of adsorbent with continuous counter-current flow of a liquid feed over the adsorbent. Feed and products enter and leave adsorbent beds continuously, at nearly constant compositions. Separation is accomplished by exploiting the differences in affinity of the adsorbent for para-xylene relative to the other $C_8$ aromatic isomers. More specifically, the adsorbent is selected for its initial affinity for para-xylene relative to the other $C_8$ aromatic isomers.

In order to desorb the para-xylene, a desorbent is used for which the adsorbent has a higher affinity relative to para-xylene. One such desorbent is para-diethylbenzene, a heavy desorbent, and which is two carbon numbers heavier than the xylenes. It is also known to use toluene, a light desorbent, which is only one carbon number lighter than the xylene feed. As a desorbent, toluene is comparatively weaker than para-diethylbenzene. Since the toluene is weaker, it requires a higher desorbent to feed ratio (D/F) and more energy for separation in extract and raffinate fractional distillation columns.

A typical SMB adsorptive process for producing para-xylene produces a single extract stream enriched in para-xylene and a single raffinate stream containing the remaining ethylbenzene, meta-xylene, and ortho-xylene from the feed. It is also possible to take two raffinate streams from the process as disclosed in U.S. 20150087878A1 and U.S. 20150266794A1 resulting in one raffinate which is enriched in ethylbenzene and the other which is enriched in meta-xylene and ortho-xylene. These two streams preferentially enriched or depleted in ethylbenzene can then be processed downstream separately, such as in separate xylene isomerization units, to take advantage of the C8 aromatic compositional differences.

More recently, U.S. Pat. No. 9,850,186B2 has shown that the two raffinates can be taken such that differences in both the C8 aromatic and toluene desorbent compositions are observed. These two raffinates are then processed separately with the desorbent-lean raffinate passing directly to a separate xylene isomerization unit from the desorbent-rich raffinate stream. While possible, this configuration requires the construction of two separate xylene isomerization units and use of toluene as a desorbent as well as the enrichment of different C8 aromatic species to take full advantage of the configuration.

Figure 1A:
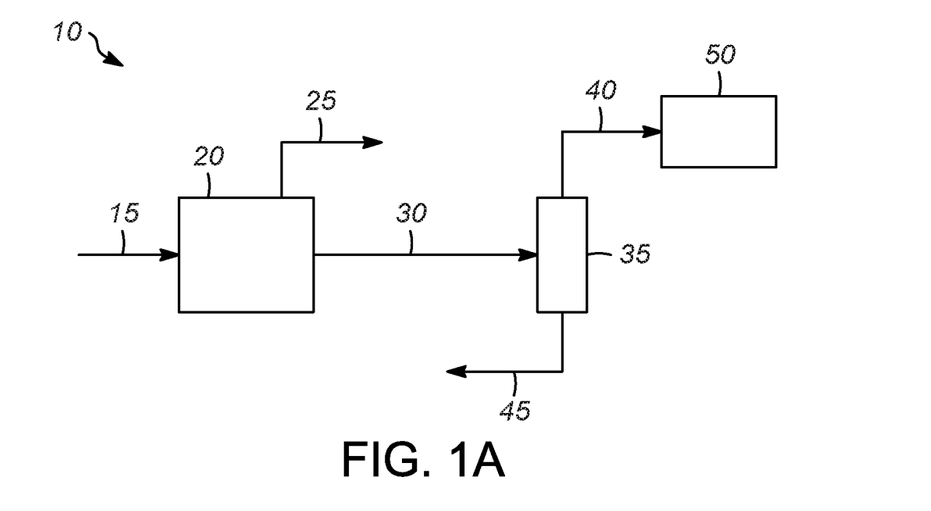
FIGS. 1A and 1B show process flow diagrams of prior art processes for producing para-xylene.
Figure 1B:
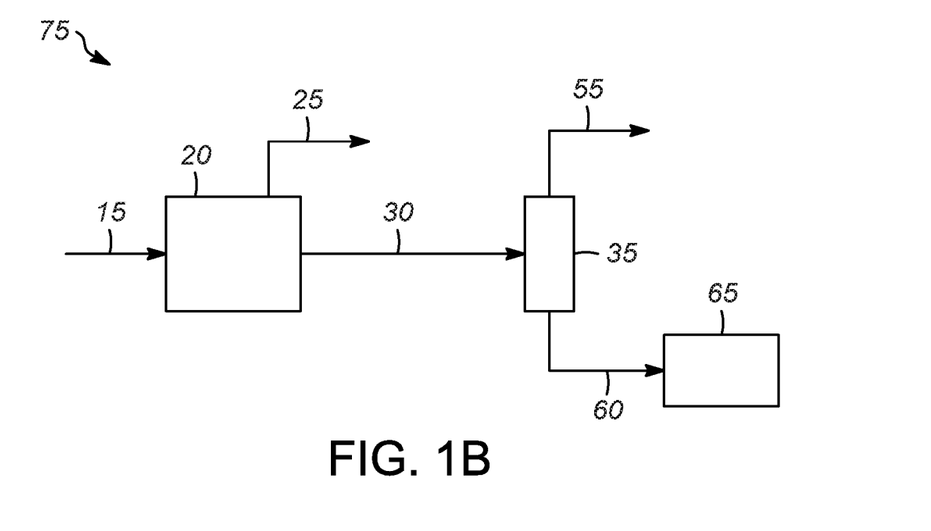

FIGS. 1A and 1B illustrate separation processes using a single raffinate stream with light and heavy desorbents. FIG. 1A shows an adsorption separation process 10 using a single raffinate stream and a heavy desorbent. The $C_8$ aromatics feed stream 15 is sent to the adsorption separation unit 20. A para-xylene extract stream 25 is recovered from the adsorption separation unit 20. A raffinate stream 30 comprising desorbent and the other $C_8$ aromatics (ethylbenzene, meta-xylene and ortho-xylene) is sent to fractional distillation column 35 where it is separated into an overhead stream 40 comprising the other $C_8$ aromatics and a bottom stream 45 comprising the desorbent. The bottom stream 45 is recycled to the adsorption separation unit 20. The overhead stream 40 is sent to an isomerization unit 50 where the $C_8$ aromatics are isomerized to produce additional para-xylene.

In FIG. 1B, a light desorbent is used in process 75. In this case, the raffinate stream 30 is separated into an overhead stream 55 comprising the desorbent and a bottom stream 60 comprising the other $C_8$ aromatics. The bottom stream 60 is sent to the isomerization unit 65.

Because fractionation is one of the largest energy users in an aromatics complex, it would be desirable to reduce the fractionation costs.

Therefore, there is a need for an improved process for producing p-xylene having reduced operating costs.

DETAILED DESCRIPTION OF THE DRAWINGS

In the drawings of the present invention, one or more embodiments are shown in which like numerals denote like elements and in which.

DEFINITIONS

As used herein, the term "stream" can include various hydrocarbon molecules and other substances.

As used herein, the term "stream", "feed", "product", "part" or "portion" can include various hydrocarbon molecules, such as straight-chain and branched alkanes, naphthenes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

As used herein, the term "overhead stream" can mean a stream withdrawn at or near a top of a vessel, such as a column.

As used herein, the term "bottoms stream" can mean a stream withdrawn at or near a bottom of a vessel, such as a column.

Hydrocarbon molecules may be abbreviated C1, C2, C3, Cn where "n" represents the number of carbon atoms in the one or more hydrocarbon molecules or the abbreviation may be used as an adjective for, e.g., non-aromatics or compounds. Similarly, aromatic compounds may be abbreviated A6, A7, A8, An where "n" represents the number of carbon atoms in the one or more aromatic molecules. Furthermore, a superscript "+" or "−" may be used with an abbreviated one or more hydrocarbons notation, e.g., C3+ or C3−, which is inclusive of the abbreviated one or more hydrocarbons. As an example, the abbreviation "C3+" means one or more hydrocarbon molecules of three or more carbon atoms.

As used herein, the term "unit" can refer to an area including one or more equipment items and/or one or more sub-zones. Equipment items can include, but are not limited to, one or more reactors or reactor vessels, separation vessels, adsorbent chamber or chambers, rotary valves, distillation towers, heaters, exchangers, pipes, pumps, compressors, and controllers. Additionally, an equipment item, such as a reactor, dryer, adsorbent chamber or vessel, can further include one or more zones or sub-zones.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top or overhead pressure is the pressure of the overhead vapor at the vapor outlet of the column. The bottom temperature is the liquid bottom outlet temperature. Overhead lines and bottoms lines refer to the net lines from the column downstream of any reflux or reboil to the column unless otherwise shown. Stripping columns omit a reboiler at a bottom of the column and instead provide heating requirements and separation impetus from a fluidized inert media such as steam.

As depicted, process flow lines in the figures can be referred to interchangeably as, e.g., lines, pipes, feeds, gases, products, discharges, parts, portions, or streams.

The term "passing" means that the material passes from a conduit or vessel to an object.

The terms "application" and "program" refer to one or more computer programs, software components, sets of instructions, procedures, functions, objects, classes, instances, related data, or a portion thereof adapted for implementation in a suitable computer code (including source code, object code, or executable code). The term "communicate," as well as derivatives thereof, encompasses both direct and indirect communication.

The "control system" is defined as hardware and software computing components that determines the set points of control elements in the adsorption section.

DESCRIPTION OF THE INVENTION

The following Description is merely exemplary in nature and is not intended to limit the invention or the application and uses of the invention. Furthermore, there is no intention to be bound by any theory presented in the preceding Background or the following Description.

Adsorptive separation is applied to the recovery of a variety of hydrocarbon and other chemical products. Chemical separations using this approach which have been disclosed include the separation of mixtures of aromatics into specific aromatic isomers, of linear from nonlinear aliphatic and olefinic hydrocarbons, of either paraffins or aromatics from a feed mixture comprising both aromatics and paraffins, of chiral compounds for use in pharmaceuticals and fine chemicals, of oxygenates such as alcohols and ethers, and of carbohydrates such as sugars. Aromatics separations include mixtures of dialkyl-substituted monocyclic aromatics and of dimethyl naphthalenes. A major commercial application, which forms the focus of the prior references and of the following description of the present invention, without so limiting it, is the recovery of para-xylene and/or meta-xylene from mixtures of $C_8$ aromatics.

The invention normally is employed in an adsorptive separation process which simulates countercurrent movement of the adsorbent and surrounding liquid as described above.

Fractionation in the para-xylene production process is one of the largest energy users in a modern aromatics complex. Therefore, reducing the fractionation costs leads to improved economics.

It was demonstrated from modeling that using two raffinate streams from the adsorption process yields significantly different stream compositions with respect to the desorbent, as demonstrated in Example 1 below.

Using the dual raffinate approach, two streams are fed to the raffinate column independently to take advantage of the differing desorbent concentrations. When this is done, and additional stages are added between the two feed trays in the raffinate column, it results in significant reboiler duty savings and a reduction in overall fired fuel needed.

In the prior art, patents utilizing two raffinate streams are focused on the compositional differences in the $C_8$ aromatic isomers (i.e., the components in the feed that are being separated in the process) in each raffinate stream. They involve the use of separate raffinate columns and/or separate isomerization units, resulting in significantly increased capital costs.

In contrast, the present invention focuses on the difference in the amount of desorbent in the two raffinate streams and sending those streams to a single fractionation column and a single isomerization, which reduces the capital costs of the system.

One aspect of the invention is a process for producing para-xylene. In one embodiment, the process comprises separating a mixture of $C_8$ aromatic isomers in a simulated moving bed apparatus using a desorbent to produce a para-xylene-rich extract stream, a desorbent-rich raffinate stream, and a desorbent-lean raffinate stream, wherein a concentration of desorbent in the desorbent-rich raffinate stream is greater than a concentration of desorbent in the desorbent-lean raffinate stream. The desorbent-rich raffinate stream and the desorbent-lean raffinate stream are introduced into a fractional distillation column having a $C_8$ aromatic outlet and a desorbent outlet, wherein the desorbent-rich raffinate stream is introduced at a first feed tray and wherein the desorbent-lean raffinate stream is introduced at a second feed tray, and wherein the first feed tray is closer to the desorbent outlet than the second feed tray. The desorbent-rich raffinate stream and the desorbent-lean raffinate stream are separated in the fractional distillation column into a $C_8$ aromatic stream and a desorbent stream.

In some embodiments, the process further comprises: introducing the $C_8$ aromatic stream from the fractional distillation column into an isomerization zone; and isomerizing the $C_8$ aromatic stream to form an isomerized $C_8$ aromatic stream.

In some embodiments, the process further comprises: recycling the isomerized $C_8$ aromatic stream into the simulated moving bed apparatus and wherein the isomerized aromatic stream comprises at least a portion of the mixture $C_8$ aromatic isomers.

In some embodiments, the process further comprises: recycling the desorbent stream from the fractional distillation column to the simulated moving bed apparatus and wherein the recycled desorbent stream comprises at least a portion of the desorbent in the simulated moving bed apparatus.

In some embodiments, the desorbent is a light desorbent and wherein the $C_8$ aromatic outlet is a bottom outlet and the desorbent outlet is an overhead outlet.

In some embodiments, the light desorbent comprises toluene.

In some embodiments, the first feed tray is separated from the second feed tray by 5-15 stages.

In some embodiments, the desorbent is a heavy desorbent and wherein the $C_8$ aromatic outlet is an overhead outlet and the desorbent outlet is a bottom outlet.

In some embodiments, the heavy desorbent comprises paradiethylbenzene.

In some embodiments, the first feed tray is separated from the second feed tray by 25-30 stages.

In some embodiments, the desorbent-rich raffinate stream comprises 45-65 wt % desorbent and the desorbent-lean raffinate stream comprises 10-35 wt % desorbent.

In some embodiments, the process further comprises at least one of: sensing at least one parameter of the process and generating a signal or data from the sensing; generating and transmitting a signal; or generating and transmitting data.

Another aspect of the invention is a process for producing para-xylene. In one embodiment, the process comprises: separating a mixture of $C_8$ aromatic isomers in a simulated moving bed apparatus using a desorbent to produce a para-xylene-rich extract stream, a desorbent-rich raffinate stream, and a desorbent-lean raffinate stream, wherein a concentration of desorbent in the desorbent-rich raffinate stream is greater than a concentration of desorbent in the desorbent-lean raffinate stream. The desorbent-rich raffinate stream and the desorbent-lean raffinate stream are introduced directly into a fractional distillation column having a $C_8$ aromatic outlet and a desorbent outlet, wherein the desorbent-rich raffinate stream is introduced at a first feed tray and wherein the desorbent-lean raffinate stream is introduced at a second feed tray, and wherein the first feed tray is closer to the desorbent outlet than the second feed tray. The desorbent-rich raffinate stream and the desorbent-lean raffinate stream are separated in the fractional distillation column into an aromatic stream and a desorbent stream. The $C_8$ aromatic stream from the fractional distillation column is introduced into an isomerization zone. The $C_8$ aromatic stream is isomerized to form an isomerized aromatic stream. The isomerized $C_8$ aromatic stream is recycled to the simulated moving bed apparatus and wherein the isomerized $C_8$ aromatic stream comprises at least a portion of the mixture $C_8$ aromatic isomers.

In some embodiments, the process further comprises: recycling the desorbent stream from the fractional distillation column to the simulated moving bed apparatus and wherein the recycled desorbent stream comprises at least a portion of the desorbent in the simulated moving bed apparatus.

In some embodiments, the desorbent is a light desorbent and wherein the $C_8$ aromatic outlet is a bottom outlet and the desorbent outlet is an overhead outlet.

In some embodiments, the first feed tray is separated from the second feed tray by 5-15 stages.

In some embodiments, the desorbent is a heavy desorbent and wherein the $C_8$ aromatic outlet is an overhead outlet and the desorbent outlet is a bottom outlet.

In some embodiments, the first feed tray is separated from the second feed tray by 25-30 stages.

In some embodiments, the desorbent-rich raffinate stream comprises 45-65 wt % desorbent and the desorbent-lean raffinate stream comprises 10-35 wt % desorbent.

In some embodiments, the desorbent comprises a light desorbent comprising toluene, or the desorbent comprises a heavy desorbent comprising paradiethylbenzene.

Figure 2A:
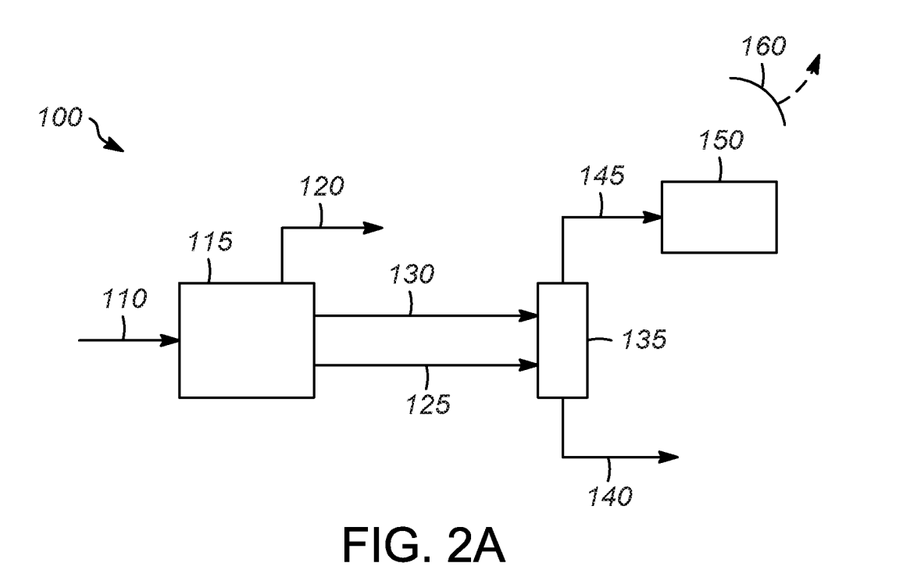
FIGS. 2A and 2B show process flow diagrams of processes for producing para-xylene according to one or more embodiments of the present invention.
Figure 2B:
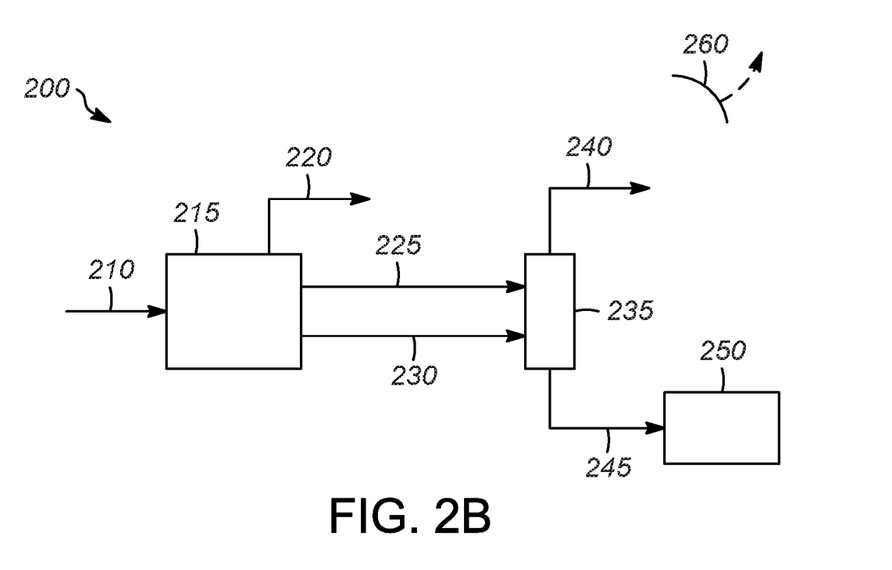

FIGS. 2A and 2B illustrate separation processes using the two raffinate stream approach of the present invention with light and heavy desorbents. Light desorbents have a carbon number less than the xylenes, while a heavy desorbent has a carbon number greater than the xylenes.

As shown in FIG. 2A, when a heavy desorbent is used in process 100, the desorbent is taken off the bottom of the column. Suitable heavy desorbents include, but are not limited to, paradiethylbenzene. In this case, the main raffinate, which contains the most desorbent, is located closer to the bottom of the column.

The $C_8$ aromatics feed stream 110 is sent to the adsorption separation unit 115 in which the para-xylene is separated from xylene mixture using a SMB unit. The SMB process is a commercial adsorptive separation process using several adsorption beds and moving the inlet streams and outlet streams between the beds, where a process stream comprising para-xylene is passed through the beds. The adsorption beds comprise an adsorbent for preferentially adsorbing the para-xylene and later desorbing the para-xylene using a desorbent as the process stream. As is known in the art, SMB technology is an established commercial technology wherein beds of the adsorbent are held in place in one or more typically cylindrical adsorbent chambers and the positions at which the streams involved in the process enter and leave the chambers are slowly shifted along the length of the chambers. Normally, there are at least four streams (feed, desorbent, extract, and raffinate) employed in this procedure and the location at which the feed and desorbent streams enter the chamber via individual bedlines and the extract and raffinate streams leave the chamber via other bedlines are simultaneously shifted in the same direction at set intervals. Each shift in location of these transfer points delivers or removes liquid from a different bed within the adsorbent chamber. This shifting could be performed using a dedicated bedline for each stream at the entrance to each bed. However, a large scale simulated moving bed technology process unit will normally have at least eight separate beds, or at least twelve separate beds, or at least sixteen separate beds or as many as twenty-four separate beds. Employing a separate bedline for each stream at each bed would greatly increase the cost of the process and therefore the bedlines are reused with each bedline carrying one of the four process streams at some point in the cycle and a valve, such as a rotary valve, controlling the flow of the four streams throughout the unit.

A SMB process produces at least two effluent streams: an extract stream containing a compound which was selectively retained on the adsorbent; and, a raffinate stream containing compounds not strongly adsorbed. Both the extract and the raffinate streams will also contain the desorbent. The concentration of the desorbent in the extract and raffinate stream will vary somewhat with time during each incremental shifting of the process bed lines. The extract and raffinate streams typically are passed into extract and raffinate fractional distillation columns, in which the desorbent is separated from the extract and raffinate compounds, respectively. The desorbent is in this way recovered, and it may be then recycled to the adsorption zone as a process stream referred to herein as the desorbent stream. Each bed will include an adsorbent, discussed in more detail below.

The adsorbent preferentially adsorbs para-xylene while permitting meta-xylene, ortho-xylene, and ethylbenzene to essentially pass through in an unchanged condition and become part of a raffinate stream. Thereafter, the adsorbed para-xylene is desorbed from the adsorbent by passing a desorbent through the adsorbent bed, forming an extract stream. The desorbent material is commonly also used to flush non-adsorbed materials from the void spaces around and within the adsorbent.

The adsorption and desorption steps can be performed in a single large bed of adsorbent or in several parallel beds on a swing bed basis. However, it has been found that simulated moving bed adsorptive separation provides several advantages, such as high purity and recovery. Therefore, many commercial scale petrochemical separations, especially those for the separation of xylenes and mixed normal paraffins are performed using SMB technology. Further details on equipment and techniques for using in an SMB process may be found in U.S. Pat. Nos. 3,208,833; 3,214,247; 3,392,113; 3,455,815; 3,523,762; 3,617,504; 4,006,197; 4,133,842; 4,434,051; and other patents.

A para-xylene extract stream 120 is removed from the adsorption separation unit 115 and can be processed further as desired.

A desorbent rich raffinate stream 125 comprising desorbent and the other $C_8$ aromatics is sent to fractional distillation column 135. The term "rich" is intended to indicate a concentration of the indicated compound or class of compounds greater than 45 wt %, or in the range of 45-65 wt %. A desorbent lean raffinate stream 130 comprising desorbent and the other $C_8$ aromatics is also sent fractional distillation column 135. The term "lean" is intended to indicate a concentration of the indicated compound or class of compounds less than 35 wt %, or in the range of 10-35%.

The desorbent rich raffinate stream 125 contains more desorbent than the desorbent lean stream 130. Consequently, desorbent rich raffinate stream 125 enters the fractional distillation column closer to the bottom stream 140 comprising desorbent than the desorbent lean raffinate stream 130.

The desorbent rich raffinate stream 125 feed tray is separated from the desorbent lean raffinate stream 130 by 25-30 stages.

The desorbent rich raffinate stream 125 and the desorbent lean raffinate stream 130 are separated into a bottom stream 140 comprising the desorbent and an overhead stream 145 comprising the other $C_8$ aromatics. The bottom stream 140 is recycled to the adsorption separation unit 115. The bottom stream 140 contains 98 wt % or more heavy desorbent, or 98.5 wt % or more, or 99 wt % or more, or 99.5 wt % or more. The overhead stream 145 is sent to an isomerization unit 150 to be isomerized into more desirable aromatics, including para-xylene.

In the process 200 shown FIG. 2B, a light desorbent is used. When a light desorbent is used, the stream with more desorbent is fed closer to the top of the column because desorbent is taken as an overhead and the $C_8$ aromatics are taken as the bottom stream. In this case, the desorbent rich raffinate stream 225 is closer to the overhead stream than the desorbent lean raffinate stream 230. The desorbent rich raffinate stream 225 feed tray is separated from the desorbent lean raffinate stream 230 feed tray by 5-15 stages.

The desorbent rich raffinate stream 225 and the desorbent lean raffinate stream 130 are separated into an overhead stream 240 comprising the desorbent and a bottom stream 245 comprising the other $C_8$ aromatics. The bottom stream 245 is sent to the isomerization unit 250. The overhead stream 240 contains 95 wt % or more light desorbent, or 96 wt % or more, or 97 wt % or more, or 98 wt % or more, or 99 wt % or more, or 99.5% or more.

The description of the process and apparatus of the prior art and this invention are presented with reference to the attached Figures. The Figures are simplified diagrams of the prior art and various embodiments of the present invention and are not intended as an undue limitation on the generally broad scope of the description provided herein and the appended claims. Certain hardware such as valves, pumps, compressors, heat exchangers, instrumentation and controls, have been omitted as not essential to a clear understanding of the invention. The use and application of this hardware is well within the skill of the art.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect. FIGS. 2A and 2B show the above categorically as 160, 260.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

Example 1

The separation system was modeled using a computer modeling program based on the following feed and desorbent compositions and flowrates, an operating temperature of 156° C. (312° F.), and a cycle time of 34 min. using a typical zeolite-type adsorbent known to those in the art for separating and purifying para-xylene.

|  | Flowrate | Composition, wt % | | | | | |
|---|---|---|---|---|---|---|---|
|  |  | pX | EB | mX | oX | Sat | Tol |
| Feed | 90 | 22.4 | 12.3 | 52.0 | 5.3 | 0.0 | 7.9 |
| Desorbent | 160 | 0.8 | 0.0 | 0.0 | 0.0 | 0.5 | 98.7 |

As shown in Table 1, when a two raffinate stream system is used, the main raffinate stream contains about 60 wt % desorbent, while the second raffinate stream contains about 30 wt % desorbent. If these two streams are mixed together, as would be the case for a single raffinate design, the resulting stream would contain about 50 wt % desorbent. By feeding the two streams separately to a single raffinate column and adding five stages between the two feeds, the reboiler duty of the column is reduced by 3.9% relative to the single raffinate case.

TABLE 1

Case 1 - two separate raffinate streams to single raffinate column

| | | Composition, wt % | | | |
|---|---|---|---|---|---|
| | Flowrate | pX | EB | mX | oX | Tol |
| Raffinate 1 | 119 | 1.1 | 6.4 | 29.9 | 3.2 | 59.2 |
| Raffinate 2 | 40 | 2.8 | 13.6 | 50.0 | 4.8 | 28.7 |

Case 2 - single combined raffinate stream to single raffinate column

| | | Composition, wt % | | | |
|---|---|---|---|---|---|
| | Flowrate | pX | EB | mX | oX | Tol |
| Raffinate | 158 | 1.5 | 8.2 | 34.9 | 3.6 | 51.6 |

Example 2

The two raffinate system was also investigated experimentally using a simulated moving bed pilot plant and paradiethylbenzene desorbent. The pilot plant was operated at 177° C. (350° F.) and 27 min cycle time, and used a zeolite-based adsorbent known to those in the art to be suitable for separating and purifying para-xylene. The feed and desorbent rates and compositions for this experiment were as follows:

| | | Composition, wt % | | | |
|---|---|---|---|---|---|
| | Flowrate | pX | EB | mX | oX | pDEB |
| Feed | 633 | 22.3 | 7.0 | 48.7 | 21.8 | 0.0 |
| Desorbent | 784 | 0.0 | 0.0 | 0.0 | 0.0 | 99.1 |

The resulting raffinate compositions when 25.5% of the overall raffinate is taken as a second raffinate is shown in Table 2. Table 2 shows the substantially different paradiethylbenzene compositions in the two raffinates. The $C_8$ aromatic compositions of the two raffinates are similar once the desorbent is fractionated away from the stream as would be done in a downstream raffinate column. By feeding the two raffinates separately to a single raffinate column and adding twenty stages between the feeds, the reboiler duty is reduced by 1.8% relative to the single raffinate case.

TABLE 2

| | | Composition, wt % | | | |
|---|---|---|---|---|---|
| | Flowrate | pX | EB | mX | oX | pDEB |
| Raffinate 1 | 833 | 0.6 | 2.5 | 22.5 | 10.2 | 63.8 |
| Raffinate 2 | 286 | 1.7 | 6.0 | 40.7 | 18.0 | 33.3 |

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

SPECIFIC EMBODIMENTS

While the following is described in conjunction with specific embodiments, it will be understood that this description is intended to illustrate and not limit the scope of the preceding description and the appended claims.

A first embodiment of the invention is a process for producing para-xylene comprising separating a mixture of $C_8$ aromatic isomers in a simulated moving bed apparatus using a desorbent to produce a para-xylene-rich extract stream, a desorbent-rich raffinate stream, and a desorbent-lean raffinate stream, wherein a concentration of desorbent in the desorbent-rich raffinate stream is greater than a concentration of desorbent in the desorbent-lean raffinate stream; introducing the desorbent-rich raffinate stream and the desorbent-lean raffinate stream into a fractional distillation column having a $C_8$ aromatic outlet and a desorbent outlet, wherein the desorbent-rich raffinate stream is introduced at a first feed tray and wherein the desorbent-lean raffinate stream is introduced at a second feed tray, and wherein the first feed tray is closer to the desorbent outlet than the second feed tray; and separating the desorbent-rich raffinate stream and the desorbent-lean raffinate stream in the fractional distillation column into a $C_8$ aromatic stream and a desorbent stream. An embodiment of the invention is one, any or all of prior embodiments in this paragraph up through the first embodiment in this paragraph further comprising introducing the $C_8$ aromatic stream from the fractional distillation column into an isomerization zone; and isomerizing the $C_8$ aromatic stream to form an isomerized $C_8$ aromatic stream. An embodiment of the invention is one, any or all of prior embodiments in this paragraph up through the first embodiment in this paragraph further comprising recycling the isomerized $C_8$ aromatic stream into the simulated moving bed apparatus and wherein the isomerized aromatic stream comprises at least a portion of the mixture $C_8$ aromatic isomers. An embodiment of the invention is one, any or all of prior embodiments in this paragraph up through the first embodiment in this paragraph further comprising recycling the desorbent stream from the fractional distillation column to the simulated moving bed apparatus and wherein the recycled desorbent stream comprises at least a portion of the desorbent in the simulated moving bed apparatus. An embodiment of the invention is one, any or all of prior embodiments in this paragraph up through the first embodiment in this paragraph wherein the desorbent is a light desorbent and wherein the $C_8$ aromatic outlet is a bottom outlet and the desorbent outlet is an overhead outlet. An embodiment of the invention is one, any or all of prior embodiments in this paragraph up through the first embodiment in this paragraph wherein the light desorbent from the overhead outlet comprises toluene. An embodiment of the invention is one, any or all of prior embodiments in this paragraph up through the first embodiment in this paragraph wherein the first feed tray is separated from the second feed tray by 5-15 stages. An embodiment of the invention is one, any or all of prior embodiments in this paragraph up through the first embodiment in this paragraph wherein the desorbent is a heavy desorbent and wherein the $C_8$ aromatic outlet is an overhead outlet and the desorbent outlet is a bottom outlet. An embodiment of the invention is one, any or all of prior embodiments in this paragraph up through the first embodiment in this paragraph wherein the heavy desorbent from the bottom outlet comprises paradiethylbenzene. An embodiment of the invention is one, any or all of prior embodiments in this paragraph up through the first embodiment in this paragraph wherein the first feed tray is separated from the second feed tray by 25-30 stages. An embodiment of the invention is one, any or all of prior embodiments in this paragraph up through the first embodiment in this paragraph wherein the desorbent-rich raffinate stream comprises 45-65 wt % desorbent and the desorbent-lean raffinate stream comprises 10-35 wt % desorbent. An embodiment of the invention is one, any or all of prior embodiments in this paragraph up through the first embodiment in this paragraph, further comprising at least one of sensing at least one parameter of the process and generating a signal or data from the sensing; generating and transmitting a signal; or generating and transmitting data.

A second embodiment of the invention is a process for producing para-xylene comprising separating a mixture of $C_8$ aromatic isomers in a simulated moving bed apparatus using a desorbent to produce a para-xylene-rich extract stream, a desorbent-rich raffinate stream, and a desorbent-lean raffinate stream, wherein a concentration of desorbent in the desorbent-rich raffinate stream is greater than a concentration of desorbent in the desorbent-lean raffinate stream; introducing the desorbent-rich raffinate stream and the desorbent-lean raffinate stream directly into a fractional distillation column having a $C_8$ aromatic outlet and a desorbent outlet, wherein the desorbent-rich raffinate stream is introduced at a first feed tray and wherein the desorbent-lean raffinate stream is introduced at a second feed tray, and wherein the first feed tray is closer to the desorbent outlet than the second feed tray; separating the desorbent-rich raffinate stream and the desorbent-lean raffinate stream in the fractional distillation column into an aromatic stream and a desorbent stream; introducing the $C_8$ aromatic stream from the fractional distillation column into an isomerization zone; isomerizing the $C_8$ aromatic stream to form an isomerized aromatic stream; and recycling the isomerized $C_8$ aromatic stream to the simulated moving bed apparatus and wherein the isomerized $C_8$ aromatic stream comprises at least a portion of the mixture $C_8$ aromatic isomers. An embodiment of the invention is one, any or all of prior embodiments in this paragraph up through the second embodiment in this paragraph further comprising recycling the desorbent stream from the fractional distillation column to the simulated moving bed apparatus and wherein the recycled desorbent stream comprises at least a portion of the desorbent in the simulated moving bed apparatus. An embodiment of the invention is one, any or all of prior embodiments in this paragraph up through the second embodiment in this paragraph wherein the desorbent is a light desorbent and wherein the $C_8$ aromatic outlet is a bottom outlet and the desorbent outlet is an overhead outlet. An embodiment of the invention is one, any or all of prior embodiments in this paragraph up through the second embodiment in this paragraph wherein the first feed tray is separated from the second feed tray by 5-15 stages. An embodiment of the invention is one, any or all of prior embodiments in this paragraph up through the second embodiment in this paragraph wherein the desorbent is a heavy desorbent and wherein the $C_8$ aromatic outlet is an overhead outlet and the desorbent outlet is a bottom outlet. An embodiment of the invention is one, any or all of prior embodiments in this paragraph up through the second embodiment in this paragraph wherein the first feed tray is separated from the second feed tray by 25-30 stages. An embodiment of the invention is one, any or all of prior embodiments in this paragraph up through the second embodiment in this paragraph wherein the desorbent-rich raffinate stream comprises 45-65 wt % desorbent and the desorbent-lean raffinate stream comprises 10-35 wt % desorbent. An embodiment of the invention is one, any or all of prior embodiments in this paragraph up through the second embodiment in this paragraph wherein the desorbent comprises a light desorbent comprising toluene, or the desorbent comprises a heavy desorbent comprising paradiethylbenzene.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for producing para-xylene comprising:
    separating a mixture of $C_8$ aromatic isomers in a simulated moving bed apparatus using a desorbent to produce a para-xylene-rich extract stream, a desorbent-rich raffinate stream, and a desorbent-lean raffinate stream, wherein a concentration of desorbent in the desorbent-rich raffinate stream is greater than a concentration of desorbent in the desorbent-lean raffinate stream;
    introducing the desorbent-rich raffinate stream and the desorbent-lean raffinate stream into a fractional distillation column having a $C_8$ aromatic outlet and a desorbent outlet, wherein the desorbent-rich raffinate stream is introduced at a first feed tray and wherein the desorbent-lean raffinate stream is introduced at a second feed tray, and wherein the first feed tray is closer to the desorbent outlet than the second feed tray; and separating the desorbent-rich raffinate stream and the desorbent-lean raffinate stream in the fractional distillation column into a $C_8$ aromatic stream and a desorbent stream.

2. The process of claim 1 further comprising:
introducing the $C_8$ aromatic stream from the fractional distillation column into an isomerization zone; and
isomerizing the $C_8$ aromatic stream to form an isomerized $C_8$ aromatic stream.

3. The process of claim 2 further comprising:
recycling the isomerized $C_8$ aromatic stream into the simulated moving bed apparatus and wherein the isomerized aromatic stream comprises at least a portion of the mixture $C_8$ aromatic isomers.

4. The process of claim 1 further comprising:
recycling the desorbent stream from the fractional distillation column to the simulated moving bed apparatus and wherein the recycled desorbent stream comprises at least a portion of the desorbent in the simulated moving bed apparatus.

5. The process of claim 1 wherein the desorbent is a light desorbent and wherein the $C_8$ aromatic outlet is a bottom outlet and the desorbent outlet is an overhead outlet.

6. The process of claim 5 wherein the light desorbent from the overhead outlet comprises toluene.

7. The process of claim 5 wherein the first feed tray is separated from the second feed tray by 5-15 stages.

8. The process of claim 1 wherein the desorbent is a heavy desorbent and wherein the $C_8$ aromatic outlet is an overhead outlet and the desorbent outlet is a bottom outlet.

9. The process of claim 8 wherein the heavy desorbent from the bottom outlet comprises paradiethylbenzene.

10. The process of claim 8 wherein the first feed tray is separated from the second feed tray by 25-30 stages.

11. The process of claim 1 wherein the desorbent-rich raffinate stream comprises 45-65 wt % desorbent and the desorbent-lean raffinate stream comprises 10-35 wt % desorbent.

12. The process of claim 1, further comprising at least one of:
sensing at least one parameter of the process and generating a signal or data from the sensing;
generating and transmitting a signal; or
generating and transmitting data.

13. A process for producing para-xylene comprising:
separating a mixture of $C_8$ aromatic isomers in a simulated moving bed apparatus using a desorbent to produce a para-xylene-rich extract stream, a desorbent-rich raffinate stream, and a desorbent-lean raffinate stream, wherein a concentration of desorbent in the desorbent-rich raffinate stream is greater than a concentration of desorbent in the desorbent-lean raffinate stream;
introducing the desorbent-rich raffinate stream and the desorbent-lean raffinate stream directly into a fractional distillation column having a $C_8$ aromatic outlet and a desorbent outlet, wherein the desorbent-rich raffinate stream is introduced at a first feed tray and wherein the desorbent-lean raffinate stream is introduced at a second feed tray, and wherein the first feed tray is closer to the desorbent outlet than the second feed tray;
separating the desorbent-rich raffinate stream and the desorbent-lean raffinate stream in the fractional distillation column into an aromatic stream and a desorbent stream;
introducing Whelk $C_8$ aromatic stream from the fractional distillation column into an isomerization zone;
isomerizing the $C_8$ aromatic stream to form an isomerized $C_8$ aromatic stream; and
recycling the isomerized $C_8$ aromatic stream to the simulated moving bed apparatus and wherein the isomerized $C_8$ aromatic stream comprises at least a portion of the mixture $C_8$ aromatic isomers.

14. The process of claim 13 further comprising:
recycling the desorbent stream from the fractional distillation column to the simulated moving bed apparatus and wherein the recycled desorbent stream comprises at least a portion of the desorbent in the simulated moving bed apparatus.

15. The process of claim 13 wherein the desorbent is a light desorbent and wherein the $C_8$ aromatic outlet is a bottom outlet and the desorbent outlet is an overhead outlet.

16. The process of claim 15 wherein the first feed tray is separated from the second feed tray by 5-15 stages.

17. The process of claim 13 wherein the desorbent is a heavy desorbent and wherein the $C_8$ aromatic outlet is an overhead outlet and the desorbent outlet is a bottom outlet.

18. The process of claim 17 wherein the first feed tray is separated from the second feed tray by 25-30 stages.

19. The process of claim 13 wherein the desorbent-rich raffinate stream comprises 45-65 wt % desorbent and the desorbent-lean raffinate stream comprises 10-35 wt % desorbent.

20. The process of claim 13 wherein the desorbent comprises a light desorbent comprising toluene, or the desorbent comprises a heavy desorbent comprising paradiethylbenzene.

* * * * *

UNITED STATES PATENT AND TRADEMARK OFFICE
CERTIFICATE OF CORRECTION

PATENT NO. : 10,703,691 B1
APPLICATION NO. : 16/265911
DATED : July 7, 2020
INVENTOR(S) : Anton Mlinar, Nikunj Patel and Jason L. Noe Page 1 of 1

It is certified that error appears in the above-identified patent and that said Letters Patent is hereby corrected as shown below:

In the Claims

Column 14, Line 16: Claim 13: Replace "Whelk" with "a"

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*